United States Patent [19]

Passarelli, Jr.

[11] Patent Number: 5,808,202
[45] Date of Patent: Sep. 15, 1998

[54] ELECTROMAGNETIC ACOUSTIC TRANSDUCER FLAW DETECTION APPARATUS

[76] Inventor: Frank Passarelli, Jr., 4634 Tam O'Shanter Dr., Westlake Village, Calif. 91362

[21] Appl. No.: 825,980

[22] Filed: Apr. 4, 1997

[51] Int. Cl.[6] .......................... G01N 29/24; G01N 29/06; G01N 29/26
[52] U.S. Cl. ............................ 73/643; 73/622; 364/507; 364/508
[58] Field of Search .............................. 73/579, 643, 620, 73/622, 623, 625, 626, 628, 640, 641; 364/507, 508

[56] References Cited

U.S. PATENT DOCUMENTS

| | | | |
|---|---|---|---|
| 3,916,699 | 11/1975 | Moran et al. | 73/623 |
| 4,122,723 | 10/1978 | Leuizzari et al. | 73/579 |
| 4,232,557 | 11/1980 | Vasile | 73/643 |
| 4,320,661 | 3/1982 | Peterson et al. | 73/643 |
| 4,450,725 | 5/1984 | Yamaguchi et al. | 73/643 |
| 4,829,823 | 5/1989 | Michel | 73/579 |
| 4,884,696 | 12/1989 | Peleg | 209/545 |
| 5,327,358 | 7/1994 | Stubbs | 364/507 |
| 5,493,511 | 2/1996 | Wincheski et al. | 364/508 |
| 5,581,037 | 12/1996 | Kwun et al. | 73/643 |

OTHER PUBLICATIONS

Ward Johnson, B.A. Auld, E. Segal and Frank Passarelli "Trapped torsional modees in solid cylinders" Published in the Journal Acoustic Society of America 100 Jul. 1, 1996, pp. 285–293.

*Primary Examiner*—Hezron E. Williams
*Assistant Examiner*—Rose M. Miller
*Attorney, Agent, or Firm*—Jack C. Munro

[57] ABSTRACT

The subject invention is a method and apparatus for detecting a flaw in a metallic structure which utilizes a plurality of electromagnetic acoustic transducers located in close proximity to, but spaced from, the metallic structure. Each transducer includes a plurality of magnets located in a spaced apart arrangement. The magnets of one transducer are not aligned, thereby angularly displaced, with the magnets of a directly adjacent transducer. The position of the north and south poles of the magnets of each transducer alternate. The metallic structure is to be moved relative to those transducers. The detection of a resonant frequency at a shifted location indicates the presence of a flaw in the metallic structure the position of which is marked by a marking device.

17 Claims, 6 Drawing Sheets

ELECTROMAGNETIC ACOUSTIC TRANSDUCER FLAW DETECTION APPARATUS

BACKGROUND OF THE INVENTION

1. Field of the Invention

The field of this invention relates to flaw detection apparatuses and more particularly to a flaw detection apparatus designed to detect flaws in moving metallic structures.

2. Description of the Prior Art

Inspection of commercially manufactured products such as steel and aluminum pipe and tube used in pressurized applications and elongated, cylindrical bar stock that is used in torquing applications, such as fasteners, is currently required under government and industry standards. Qualitative and quantitative standards controlling material properties such as strength, granularity and the presence and severity of flaws are the subject of these regulations. The presence of certain defects can affect the safety and structural integrity of the finished product and thereby the liability for use and performance of the product that is created. It is preferred that the flawed portion of the structure be removed with this flawed portion of the material to be recycled.

Once the position of the flaw is ascertained, the source of the flaw may be identified and corrected. At the present time under some of the current quality control programs, an entire production run can be rejected due to flaws in a few parts. The flaw(s) can be created during the natural fabrication of metallic structures such as production of a metallic structure within a foundry. Also, flaws can be created by the equipment and/or process utilized during manufacturing. By ascertaining the location of a flaw and determining the type of flaw, a problem with the manufacturing equipment or process can be discovered and corrected in order to minimize the generation of flawed metallic structures.

In order to determine flaws in metallic structures, there are currently utilized a variety of test techniques. Generally, these test techniques are divided into a destructive test technique or a non-destructive technique. Destructive testing, as the name implies, destroys a small portion of the metallic structure. The problem with destructive testing is that the selected part that is destroyed could very well be flawless and yet within other portions of the metallic part there may be numerous flaws. Therefore, destructive testing is a very poor way to test metallic structures.

There is a wide range of non-destructive test technologies such as eddy current, magnetic flux leakage, x-ray, ultrasonic, neutron diffraction and so forth. If possible, these non-destructive techniques are placed in the production line and are implemented to ascertain a flawed portion of a particular metallic structure during the normal production of the metallic structure. The primary advantage of non-destructive testing is the metallic structure is examined throughout and only the flawed portion is discovered leaving the unflawed portion for usage. Once a flawed portion of the metallic structure is determined, some means is employed to ascertain the location of that flaw and the metallic structure is marked accordingly.

In the past, acoustic resonance has been utilized as a non-destructive form of testing of metallic structures. The use of acoustic resonance can offer significant advantages over other prior art types of non-destructive testing technologies. However, acoustic resonance techniques of the prior art have met with limited success due to the difficulty and expense of applying such especially with the use of contact type transducers. Contact type transducers, as by their mechanical nature, affect the intrinsic resonance of the metallic structure since such actually contact the metallic structure. This leads to complex signal processing schemes such as taught by the patents of Las Alamos National Labs U.S. Pat. No. 5,062,296 and A. Migliori, et al., U.S. Pat. No. 4,976,148. These prior patents utilize a ceramic piezoelectric transducer which typically is a contact type of transducer. Anything that contacts the metallic part will inherently alter the resonance of the metallic part. This is not desirable since it is preferred to have the metallic structure resonate by itself.

SUMMARY OF THE INVENTION

Every metallic structure at some point will resonate at at least one frequency. The resonate is similar to producing a harmonic tone on the string of a violin. Vibrations are to be induced into the metallic part at an ever increasing frequency level. As the frequency level increases, the level of vibration most often will stay constant for the metallic structure. However, at a certain frequency, the amplitude of the vibration will increase dramatically. This is termed resonance. This point of resonance can be calculated mathematically. Whether the metallic structure is a pipe, tube, solid rod or even a plate, the approximate frequency of resonance can be calculated. The first step involved with this invention is to calculate this approximate frequency of resonance for the particular metallic structure. The metallic structure is then passed in close proximity to a plurality of electromagnetic acoustic transducers. At least two transducers are required. Each transducer is constructed of a plurality of magnets. Each magnet has a north pole and a south pole. The center axis interconnecting the north-south poles of each magnet is to be located substantially perpendicular to the exterior surface of the metallic structure. Within each one of the transducers the north/south pole arrangement is reversed from one magnet to another thereby alternating the position of the magnets across the transducer. Within each transducer, the magnets are equally spaced apart. The metallic structure is to be moved in a given direction past the transducers with the metallic structure located close to the transducers but slightly spaced therefrom. The transducers are located directly adjacent each other but spaced apart in a direction parallel to the given direction. Each magnet of the second transducer is located in alignment with a gap area between magnets of the first transducer again along a direction which is parallel to the given direction. The transducer coils are supplied power which when combined with the force of the magnets will cause the metallic structure to vibrate within a range that is to include the resonant frequency. This resonant frequency is for an unflawed metallic structure. The resonant frequency of the metallic structure is picked up by the transducer coils and then by the voltage/current sensors and transmitted through an analog-to-digital converter to a computer. Associated with the transducers is some form of a marking device that is capable of marking the metallic structure. This marking device is to be activated upon a flaw being detected. As the metallic structure passes by the transducers and when a flaw is detected, the resonant frequency is shifted out of the range established for an unflawed metallic structure. This shifted resonant frequency can be above the range or below the range for the unflawed metallic structure. Once this resonant frequency has exceeded the unflawed range, this is to be detected by the computer and the marking device is then to be activated placing a mark at the flawed location on the metallic structure. A very simple example of a marking device would be a spray painting apparatus.

The primary objective of the present invention is to construct an apparatus which is able to determine the precise location of flaws in a metallic structure, thereby alerting the manufacturer to not formulate a part from the metallic structure in the area of the flaw(s).

Another objective of the present invention is to construct a flaw detection apparatus which is able to detect flaws in metallic structures with the metallic structure moving at a relatively rapid rate thereby detecting flaws quickly.

DETAILED DESCRIPTION OF THE PREFERRED EMBODIMENT

Figure 1:
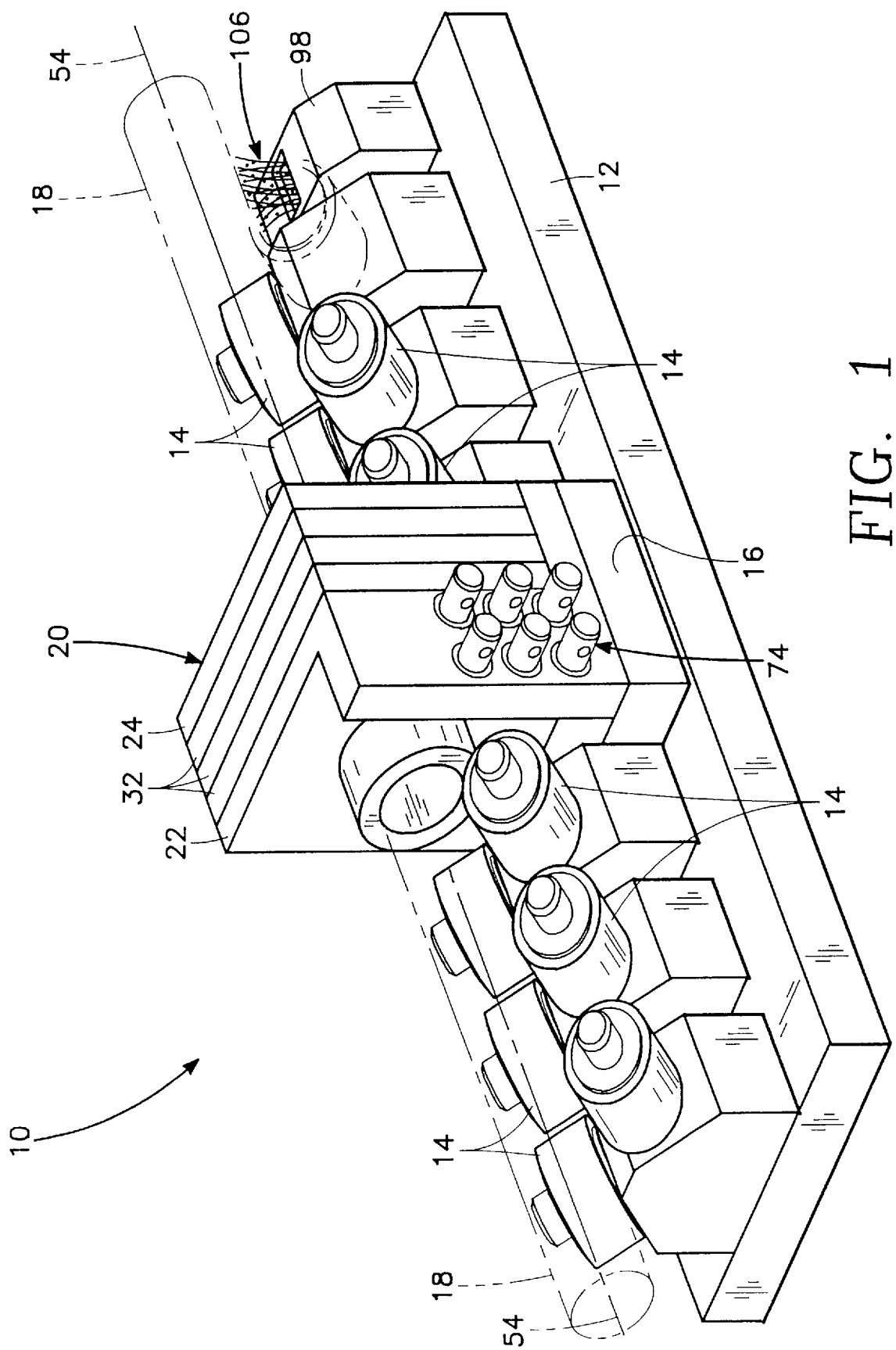
FIG. 1 is an overall view of the flaw detection apparatus of the present invention depicting a metallic structure in the form of a metal rod moving through the electromagnetic acoustic transducer assembly of the present invention showing the inclusion of a marking apparatus which is to be used to mark the position of a flaw within the metallic structure.

A novel approach of the present invention has to do with the use of the electromagnetic acoustic transducer (EMAT) that permits continuous scanning along the axis of an elongated metallic structure thus giving the flaw detection apparatus of this invention utility in a moving production line. Because the electromagnetic acoustic transducer does not contact the metallic part, distortion is thereby eliminated by the contact which would be caused by the mechanical impedance mismatch endemic to the contacting method of ultrasonic resonance generation. The use of an EMAT enables a precise segmented range or scan of vibrational frequencies of the metallic structure and its wave mode selectivity minimizes the generation of parasitic acoustic vibrations that may dilute the frequency resolution of the flaw detection system.

The use of an EMAT for the generation and detecting of resonances within metallic structures is radically different from other ultrasonic flaw detection systems. EMATs effectively address the issues of the prior art that have hindered the use of acoustic resonance in non-destructive testing. Using an EMAT for the generation of acoustic resonance provides a signal fidelity advantage of several orders of magnitude over other types of EMAT flaw detection apparatuses.

Operation of the system of the present invention takes full advantage of resonance principles. The operator, after selecting and installing the appropriate size of the transducer for the given application, enters the type of material and its shape into the computer. The software in the computer can then calculate the range of frequencies that should be subjected to the metallic structure in order to obtain a resonant frequency for the metallic structure when in an unflawed condition. The software can then control the frequency scans (through the selected range) of the transducer driving electronics. The computer then proceeds with executing, through analog electronics, a repetitive search for resonation based upon a calculation of at what frequency the metallic structure should resonate. Once resonance is established, the acceptable frequency deviations for both the unflawed condition and the flawed condition for a defect are then established and the sequential frequency and lineal scans can then proceed. The range is set for what is determined an unflawed metallic structure which establishes what is deemed to be the acceptable limits of an unflawed condition in the metallic structure. This frequency scanning rapidly divides the axis of the metallic structure under test, in the case of tubular goods or the like, into identifiable segments thus providing the ability to locate the position of any anomaly along the longitudinal axis of the tubular goods. The operator can then mark the flaw location while the testing process continues. No stopping of the metallic structure is required during the test procedure.

The principles of operation of the flaw detection apparatus of the present invention have specific utility in determining of flaws in cylindrical shapes. However, it is to be understood that the structure of this invention is not intended to be limited to only cylindrical shape geometry. Every metallic structure whose material and structural qualities are considered sound or normal will have vibrational modes that produce resonant frequencies that fall within a typical domain. Resonant behavior outside of that domain represents some range of anomalies that indicate the presence of a qualitative or quantitative defect.

In the specific case of generating vibrational modes in tubes and rods, these types of structures are mathematically treated as uniform cylinders of infinite length. While the structures under test may not fit the exact structure of a uniform cylinder of infinite length, a reasonably accurate prediction can be obtained at what frequencies the structure will resonate. The type of vibrational energy used in conjunction with this invention for flaw detection in rods and tubes comprises axial shear or axial shear-like wave modes. These axial shear vibrations are characterized by their wave vector in the azimuthal direction. The particle motion along the axial direction comprises an integral number of wavelengths around the circumference of the rod or tube. Therefore, the number of magnets incorporated within the transducer determines the number of integral wavelengths around the circumference of the rod or tube.

In order to calculate for the approximate frequency of resonance the following equation is used:

$$F = \frac{BV}{2\pi R}$$

where F equals the frequency of resonance, B equals a root value of a bessel function of a second order, V is the velocity of sound of a horizontal shear wave in the metallic structure and R is the radius of the metallic structure. The roots of a bessel function of the second order are described in the works of A. C. Erzngen and E. S. Shuhabi, *Elastodynamics*, Volume 2 (Academic, New York, N.Y., 1975) and W. Johnson, B. A. Auld and G. A. Alers, "Journal of the Acoustical Society of America", Volume 95, page 1413. Let it be assumed that in each transducer twenty-six different magnets which will produce thirteen wavelengths in the transducer. For example, let it be assumed that the metallic structure comprises an elongated length of 6061 aluminum rod having a diameter of 25.4 millimeters and which has a sound velocity (V) of 3.04 millimeters per microsecond. The first five solutions for B are shown in the following graph with the resulting frequency for resonation corresponding to each frequency. The location as to what portion of the aluminum rod these resonations occurs is also noted.

GRAPH

| B | F | Approximate Scan Depth |
| --- | --- | --- |
| 14.928374 | 576.901 KHz | From surface of rod to .20 inches deep |
| 19.883224 | 768.380 KHz | Below surface at and around .35 inches deep |
| 23.819389 | 920.491 KHz | Below surface at and around .46 inches deep |
| 27.47434 | 1,061.736 KHz | Below surface at and around .54 inches deep |
| 30.987394 | 1,197.497 KHz | Below surface at and around .60 inches deep |

It can thus be seen from the graph that if the resonant frequency is discovered around 576 KHz, flaws will be detected in the outer layer of the aluminum rod. At a frequency of about 768 KHz, flaws will be detected below the surface of the aluminum rod around a depth which corresponds to a diameter of 0.65 inches of the rod or tube. At a frequency of 920 KHz, flaws will be detected again below the surface of the rod around the depth of 0.54 inches diameter. At a frequency of 1,061 KHz, flaws will be detected below the surface of the rod around 0.46 inches in diameter. At a frequency of 1,197 KHz, flaws will be detected below the surface of the rod around 0.40 inches in diameter.

It is to be understood that the above-referenced resonant frequencies are influenced by variances in alloy composition, temperature, diameter of the rod and the presence of defects. The effect on resonance caused by the presence of defects presents a significantly different effect on the frequency causing the resonant signal to shift position in an abrupt manner. This shift in frequency is due to a decrease in the velocity of the sound being propagated through the rod. The velocity (V) of sound in a solid for shear wave is determined by the following equation:

$$V = \frac{\sqrt{\mu}}{\rho}$$

where $\mu$ is the stress and $\rho$ is the mass density. The internal stress $\mu$ is substantially affected in the vicinity of the flaw and it is reflected in the resonant frequency. Additionally, the location of the radial nodes is displaced which cause gaps in the azimuthal scan of the metal rod equal to the number of nodes as the material is scanned along its axis. In order to overcome the loss of signal that occurs due to the shifting of the nodes, the transducer is designed to generate overlapping resonant signals. This is accomplished by utilizing at least two transducers located in a side-by-side relationship. The generating of overlapping resonant signals is accomplished by locating two transducers in a side-by-side relationship with the magnets of one transducer being aligned with the gaps of the other transducer and vice versa. The second transducer is to be pivoted relative to the first transducer according to the following formula:

$$\text{angular displacement} = \frac{360°}{2X}$$

where X corresponds to the number of magnets within each of the transducers. It is to be understood that the magnets should be the same within each of the transducers. These transducers are collocated axially within the same housing and are designed to be axially stacked providing multi-channel scanning capability.

Referring to the above graph, for the user to discover flaws at the surface level of the metallic structure, it would only be necessary to use a pair of acoustic transducers which are preset to the range of around 576 KHz. However, if the user were to simultaneously determine flaws existed in the metallic structure at deeper depths, the user could utilize a second set of transducers that would operate in the range of 768 KHz which would be sensitive to flaws at and around 0.35 inches below the surface of the metallic structure. Similarly, if the user is to pick up flaws in the range at and around 0.46 inches below the surface of the metallic structure, the user only needs to use a third set of transducers that operate in the range of 920 KHz. The procedure could continue with there being a separate set of transducers for each of the operating frequencies of the aforementioned graph which would provide the user with flaw detection data substantially through the entire metallic structure.

Characteristics of the metallic structure under test such as its temperature, hardness and stress will shift the resonant frequencies from their nominal values. These characteristics will have an effect on the propagation of sound within solids by affecting the velocity of sound. Other characteristics, such as diameter variance, can also affect the resonant frequency. These characteristics need to be accounted for in order to maintain the level of frequency resolution necessary to detect material defects. All of these characteristics can be combined and treated as one since their effects combine arithmetically to shift the resonant signal. To compensate for these characteristics, an additional EMAT is added to the transducer assembly 20 by either adding a new transducer section 32 or by incorporating another electrical coil assembly within an existing transducer section 32. The purpose of this addition is to generate another acoustic resonant signal that is acoustically independent (non-interfering) from the signal that is searching for flaws and yet is "seeing" the effects of the metallic structures characteristics such as temperature upon its own velocity. An acoustically independent resonant signal can be achieved in two ways:

First the signal can be of the same type of wave mode, as for example an axial shear wave mode that is operating in a frequency of several overtones away from the frequency of the axial shear wave mode that is performing the flaw inspection operation.

The second method is to generate a wave mode that has different vibrational characteristics such as wave modes such as torsional, plane-strain, extensional and so forth. The first compensating option is implemented by scanning for one of the higher order axial shear resonances over a broader frequency (two to ten times wider) range than the flaw detection scan. Since the velocity of the shear wave can shift as much as 0.9 percent over a 100° centigrade range and smaller percentages for other material characteristics, the wider frequency scan will enable the precise determination of these effects upon the resonant frequencies of the specific wave mode. Once the resonance is established, it can be tracked at regular time intervals and the flaw detecting frequency scanning window can be adjusted by multiplying the flaw scanning signals frequency center point by the percentage change in the velocity or frequency of the temperature tracking resonances velocity or frequency term from its nominal value.

Referring particularly to the drawings, there is shown in FIG. 1 an overall view of the flaw detection apparatus 10 of this invention. The flaw detection apparatus 10 includes a base 12 on which is mounted a plurality of low frictional rollers 14. There are shown three sets of the rollers 14 located on each side of a center mount 16. However, it is considered to be within the scope of this invention that the number of the rollers 14 could be readily varied. Also, the actual usage of the rollers 14 could be optional. The sole purpose of the rollers 14 is to properly align the metallic structure 18 which is to be tested. A typical metallic structure 18 would be an elongated metal rod such as the aluminum rod which has been previously discussed.

On the center mount 16, there is mounted the electromagnetic acoustic transducer assembly 20. The electromagnetic acoustic transducer assembly 20 is composed of a face plate 22 and a backing plate 24. The face plate 22 includes a through hole 26. The backing plate 24 also includes a through hole 28. Connecting with the backing plate 24 are a series of bolts 30. The bolts 30 are to pass through the backing plate 24 and connect with the face plate 22. Tightly bound between the backing plate 24 and the face plate 22 is a plurality of transducer plates 32 each of which defines a transducer section. Each of the transducer plates 32 is identical so the same numerals will be used to describe both plates 32. It is considered to be within the scope of this invention to employ any desired number of transducer plates 32. However, for purposes of this invention, three in number of transducer sections, each of which includes a transducer plate 32, are shown.

Each transducer plate 32 includes a through hole 34. With the transducer plates 32 tightly bound in place between the face plate 22 and the backing plate 24 by the bolts 30 that are mounted within bolt receiving openings 36 mounted in the backing plate 24, the through holes 26, 28 and 34 are aligned. The metallic structure 18 is to be conductible through the through holes 26, 28 and 34. The exterior wall surface of the metallic structure 18 is spaced a slight distance from the interior wall surface of the through holes 26, 28 and 34. It is to be understood that the through holes 26, 28, and 34 are all of the same diameter. The result is that the metallic structure 18 can be moved through the through holes 26, 28 and 34 with the metallic structure 18 not coming into direct contact with the face plate 22, backing plate 24 or transducer plates 32.

Figure 5:
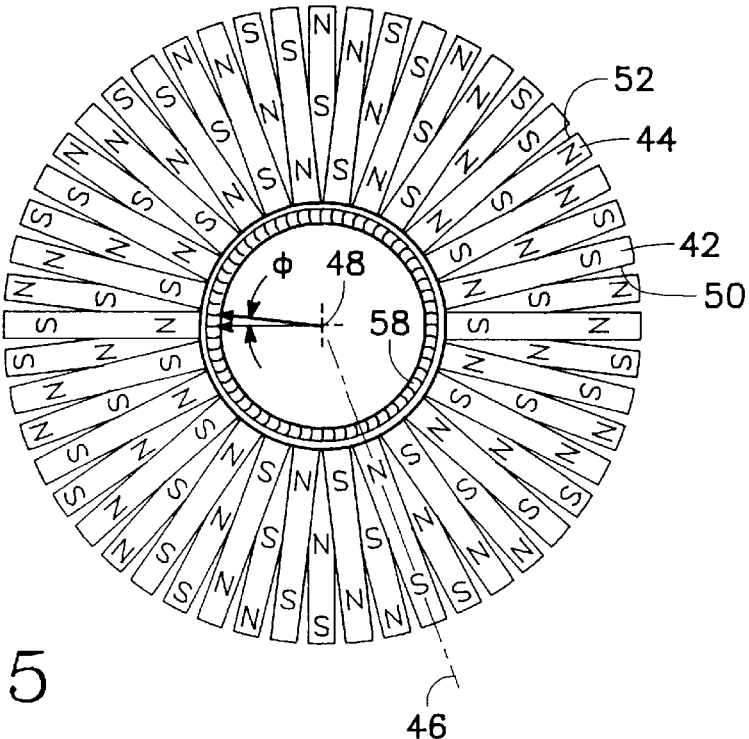
FIG. 5 is a schematic view depicting the positions of the magnets of two electromagnetic acoustic transducers.

Mounted within the transducer plate 32 is an enlarged recess 38. The enlarged recess 38 is to be concentric with the through hole 34. Mounted within the enlarged recess 38 is a mounting sleeve 40. Arranged within the mounting sleeve 40 of EMAT #1 is a plurality of magnets 42. The magnets 42 are the magnets of transducer plate 32 that are located directly adjacent the face plate 22. The magnets mounted within the transducer plate 32 that is located directly against the first mentioned transducer plate 32 will be referred to as magnets 44. Each of the magnets 42 and 44 is basically identical and each is elongated and has opposite ends with one end of which being a north pole and the other end being a south pole, as is clearly represented in FIG. 5 of the drawings. It is to be noted that there are twenty-six in number of the magnets 42 and also twenty-six in number of the magnets 44. The actual number of the magnets 42 and 44 is again deemed to be optional. It happens to be that twenty-six appears to be an optimum number of magnets for this particular usage.

Each magnet 42 and 44 has a longitudinal center axis 46. The north and south poles of each of the magnets 42 and 44 are centered on the longitudinal center axis 46. The longitudinal center axis 46 is to be positioned radially relative to the center 48 of the enlarged recess 38 which is also the center for the through hole 34. The magnets 42 are radially positioned with their outer edge located against the mounting sleeve 40. The same is true for the magnets 44. The north-south poles of the magnets 42 alternate so that when observing a magnet 42 that has its south pole located directly adjacent the through hole 34, that the magnets located directly adjacent to that south pole oriented magnet have their north poles located directly adjacent to the through hole 34. Throughout the entire annulus mounting arrangement of the magnets 42, this alternating of the poles is maintained. The same is true for the magnets 44.

It is to be noted that in between any directly adjacent pair of the magnets 42 there is an air gap 50. There is also a similar gap 52 located between the magnets 44. A magnet 44 is to be axially aligned with a gap 50. Similarly, a magnet 42 is to be axially aligned with a gap 52. It is to be understood that axially aligned means along the longitudinal center axis 54 which coincides with the center 48 and longitudinal center axis 54 of the metallic structure 18. This arrangement will result in angular displacement of the magnets 44 relative to the magnets 42. This angular displacement is represented by angle "φ" shown in FIG. 5. Since there are twenty-six magnets 42, the displacement between each of the magnets 42 will amount to 13.846 degrees. This means that the angular displacement between magnets 42 and 44 will be one-half of that amount, or 6.923 degrees.

As previously mentioned, it is important to not have gaps in the screening procedure in order to have a continuous scanning capability. It can thus be seen that when scanning there appears to be always a magnet 42 and 44 continuously around the metallic structure 18. The gaps that are inherently produced by the magnets 42 are taken up by the magnets 44. Also, the gaps that are produced by the magnets 42 and 44 are taken up by the magnets 42. Therefore, the frequency representation that is supplied to the computer will be not interrupted. If the angular displacement of the magnets 42 and 44 was not utilized, the resonant frequency representation that is transmitted to the computer would most likely be represented then disappear, then be represented, then disappear and so forth. This is not a desirable procedure since it is far more efficient to have the representation be in a constant form to supply the computer.

Mounted against the inside surface of each of the magnets 42 is a signal transmitter in the form of a coil spool 56 on which has been wound wire 58. The wire 58 has a pair of leads 60 and 62. The wire 58 would normally comprise a copper wire of a very small diameter. The size of the wire 58 is deemed to be variable and with the particular size being selected solely in accordance to individual desires. Lead 60 is to be conducted through hole 64 formed within the transducer plate 32. Lead 60 is conducted through hole 66 formed within the transducer plate 32. The leads 60 and 62 are to connect with connector 68 that is mounted within mounting hole 70 formed within the transducer plate 32. The connector 68 has a plurality of protruding, electrically connecting pins 72. Each of the leads 60 and 62 is individually electrically connected to a pair of posts 74. In a similar manner, the leads 60 and 62 for the other transducer plate 32 are electrically connected to a second pair of the posts 74. The posts 74 are mounted on the face plate 22. An O-ring 76 is used to firmly mount each connector 68 in position within the respective mounting hole 70 of each transducer plate 32.

Figure 6:
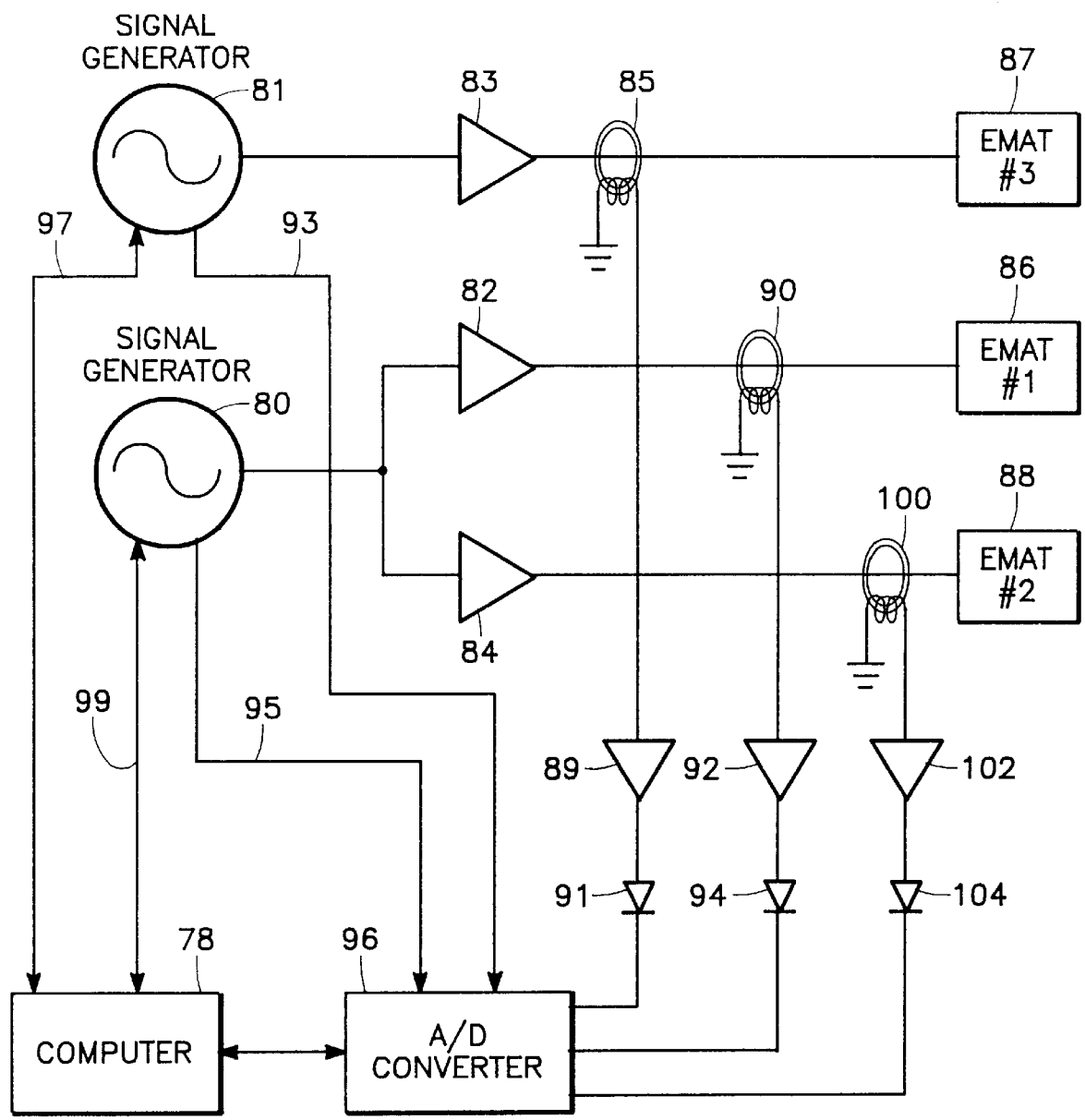
FIG. 6 is an electronic block diagram of the circuitry that is utilized to operate the flaw detection apparatus of the present invention.

Referring particularly to FIG. 6, a computer 78 is to be programmed appropriately with software for the purpose of detecting flaws within the metallic structure 18. Given the parameters for the detection of flaws, any computer programmer could design an appropriate computer program to operate with the computer 78. The computer 78 is to transmit an output signal to signal generator 80 and 81. The purpose of the signal generator 80 is to generate a sweeping sine wave upon command from the computer 78. The signal generator 80 is to be programmable. A typical signal generator 80 could be purchased from a company known as Novatech, Inc. of Seattle, Wash., part No. DDS3PC, 14 MHz precision sine wave source. The output of the signal generator 80 is to be transmitted respectively to a pair of amplifiers 82 and 84. The amplified signal from amplifier 82 is to be transmitted to EMAT #1, to the wire 58 wound on the coil spool 56, contained within the transducer plate 32 that is located directly adjacent the face plate 22. The amplifier 84 transmits a signal to EMAT #2 to the wire 58 wound on coil spool 56, that is mounted within the transducer plate 32 that is located directly adjacent the backing plate 24. It is to be understood that EMAT #1 includes the magnets 42 with EMAT #2 including magnets 44. EMAT #1 is shown as box 86 in FIG. 6 with EMAT #2 shown as box 88.

The signal that is transmitted to both EMAT #1 and EMAT #2 should be identical. As previously discussed, the projected location of the resonant signal is calculated, and let it be assumed that it is desired to determine flaws on the surface of the metallic structure 18. According to the previously shown graph, the resonation should occur at a frequency of 587 KHz. A sweeping or scanning of the signal between 586 KHz A2 and 588 KHz A2 is to occur which will result in the production of the unflawed spike shown in FIG. 7. This unflawed spike is to be picked up by means of transformer sensor 90 and supplied to an amplifier 92. From the amplifier 92 the signal is changed from a sine wave to a DC voltage by means of diode 94. The output from the diode 94 is transmitted to an analog-to-digital converter 96 which in turn transmits the signal to the computer 78. The output of the signal generator 80 is also transmitted to the counter/timer collocated on the analog-to-digital converter board of the analog-to-digital converter 96. This counter/timer circuit synchronizes the activity of the signal generator and the analog-to-digital converter 96 by keeping an accurate count of the number of cycles of each frequency step and knowing precisely when and where each step occurs in the scan (line 95 in FIG. 6).

The computer 78 is to be preprogrammed to interpret incoming data, deciphering that any spiked signal within a certain range, such as 587.2 KHz to 587.6 KHz, does not indicate a flaw within the metallic structure 18. Therefore, the marking device 98 would not be activated.

In a similar manner, the signal within EMAT #2 is monitored by a sensor 100 with this monitored signal being in the form of a sine wave transmitted to amplifier 102, and from amplifier 102, through diode 104 thereby converts the signal into a direct DC voltage. The DC voltage from diode 104 is supplied to the analog-to-digital converter 96 and then transmitted from the analog-to-digital converter 96 into the computer 78.

Figure 7:
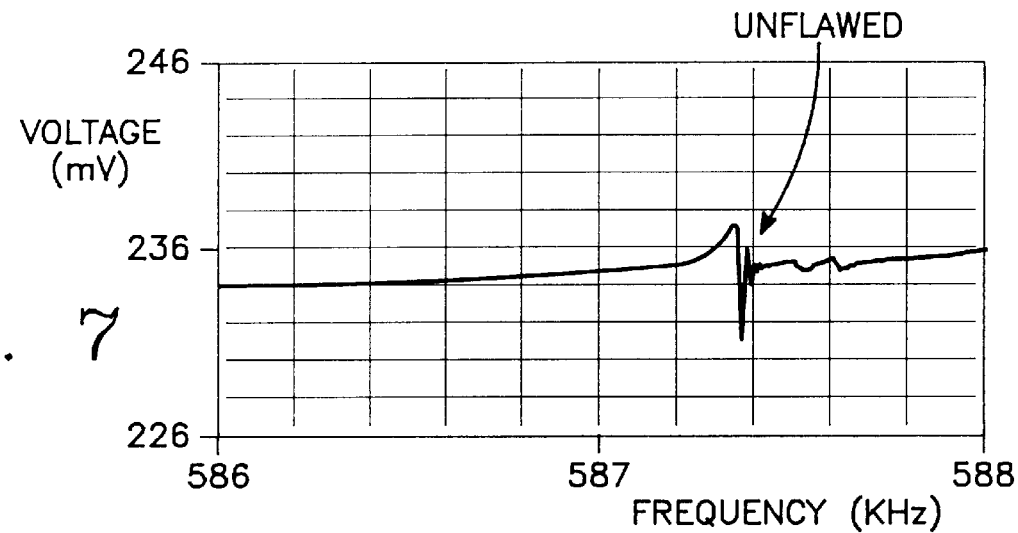
FIG. 7 is a graph of the resonant frequency of an unflawed 6061 aluminum rod of a diameter of 25.4 millimeters (mm) having a sound velocity (V) of 3.04 mm per microsecond.
Figure 8:
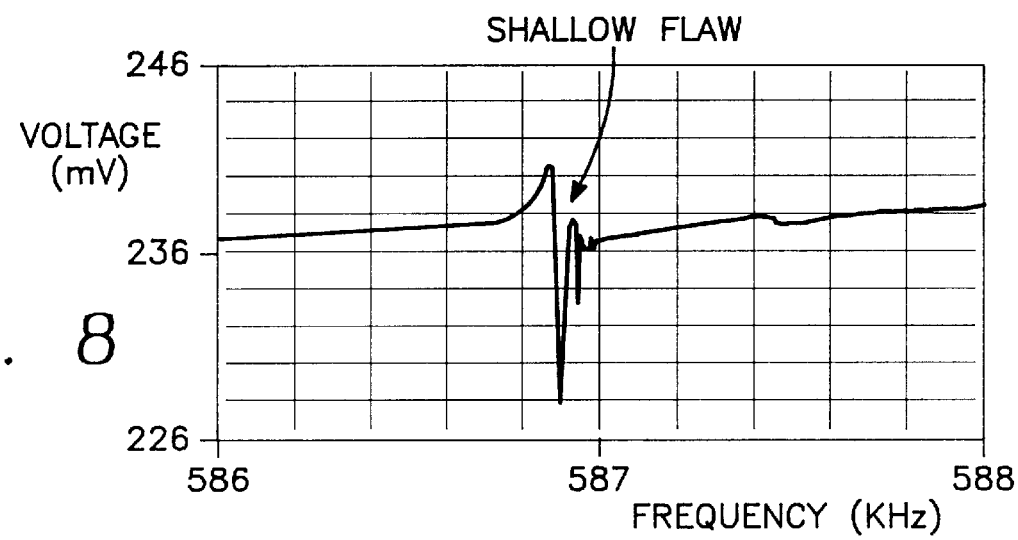
FIG. 8 is a graph of the resonant frequency for the same rod where the rod has a shallow depth flaw near or on the surface of the rod.

Let it now be assumed that a surface flaw is moved in direct proximity of EMAT #1 and EMAT #2. The spiked area of the frequency of FIG. 7 will then shift as is shown in FIG. 8 with this shift being outside the unflawed area at 587.2 KHz. The computer 78 will then document that a flaw has been detected and will appropriately cause the marking device 98 to be activated to apply a quantity of paint 106 onto the metallic structure 18. The application of the paint 106 is to correspond exactly with the location of the flaw. This flaw then will become apparent to a manufacturer that is manufacturing products from the metallic structure 18 and will then be alerted to avoid use of the flawed area of the metallic structure that is marked by the paint 106.

As previously mentioned, if the signal being transmitted to the computer 78 becomes lost due to the gap area between the magnets 42 of EMAT #1, the signal is still maintained because EMAT #2 will take over and transmit the appropriate signal to the computer 78. The reverse is also true.

Figure 9:
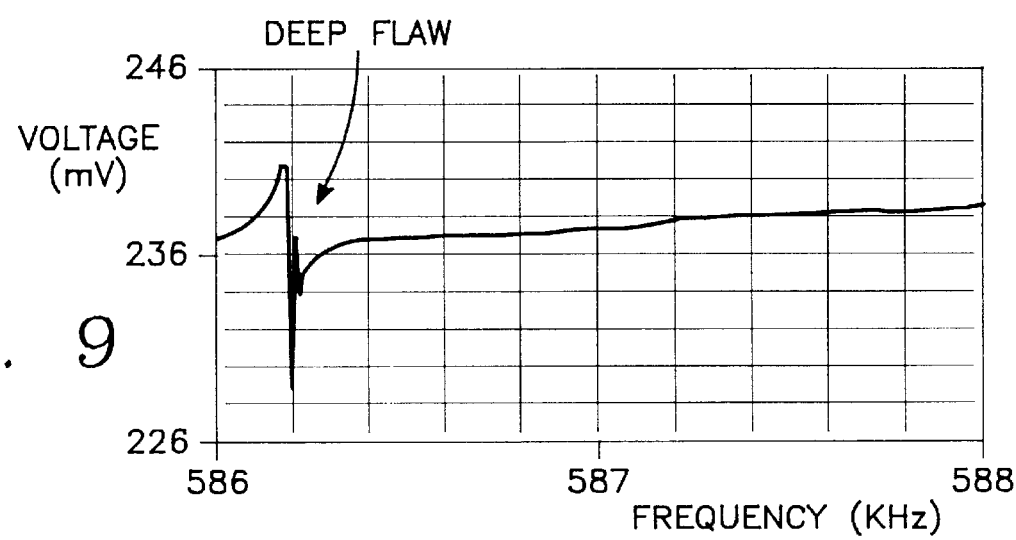
FIG. 9 is a graph of the resonant frequency for the same rod where the rod has a deeper flaw.

If the operator is looking for a deeper flaw within the metallic structure 18, a typical representation of the shift in the resonant frequency for a deeper flaw is shown in FIG. 9. It can be seen that the deeper flaw will actually cause the frequency to shift much further than the shallow flaw shown in FIG. 8.

Figure 2:
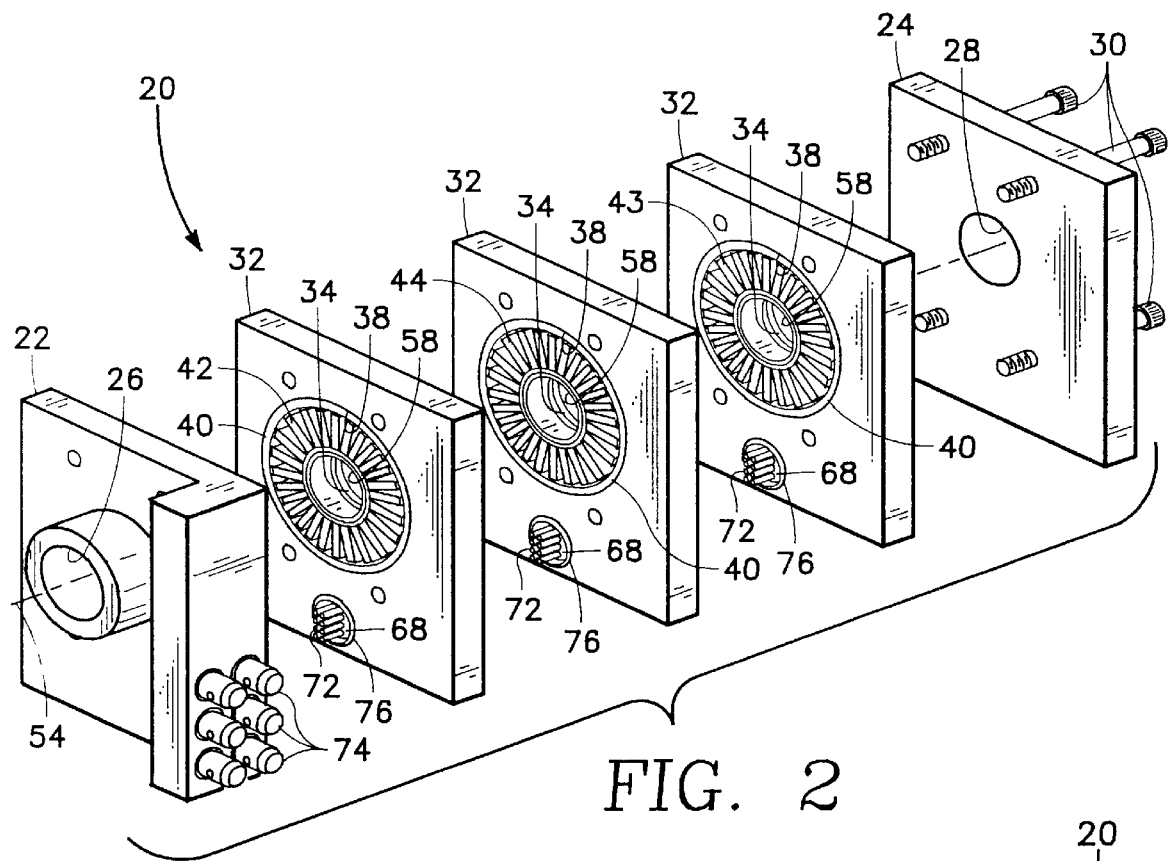
FIG. 2 is an isometric view of a basic form of an electromagnetic acoustic transducer assembly of the present invention showing the assembly in an exploded configuration.
Figure 3:
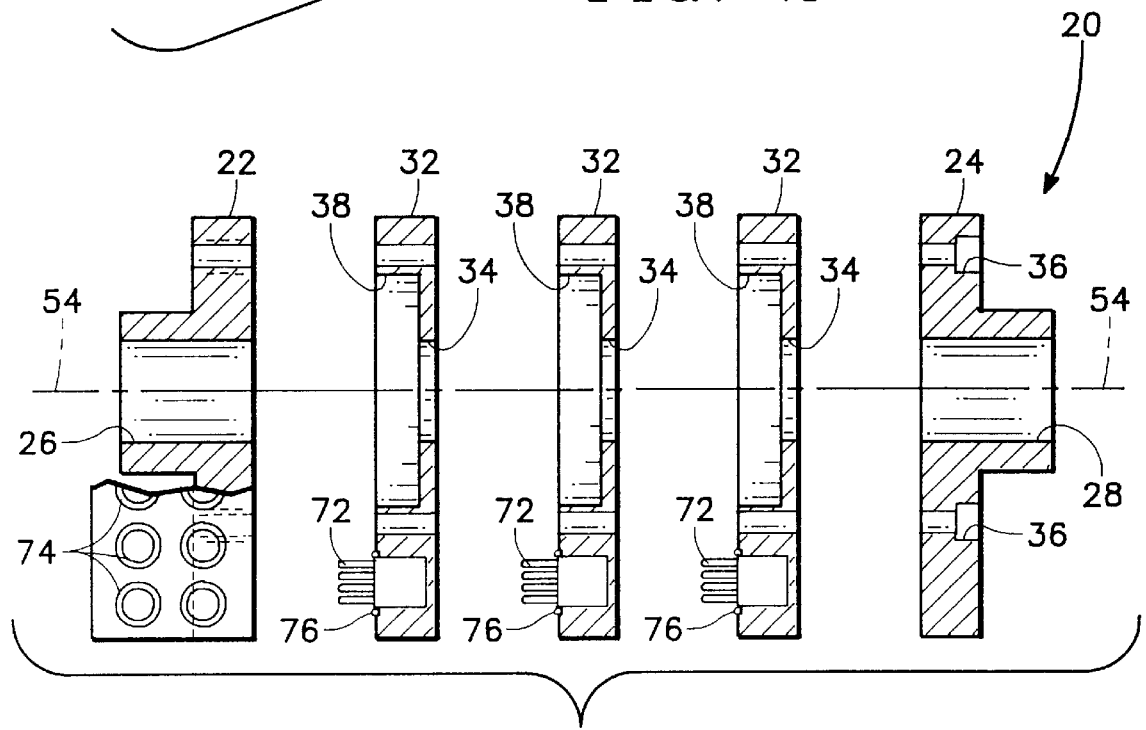
FIG. 3 is a longitudinal cross-sectional view through the electromagnetic acoustic transducer assembly of the present invention.

It is to be noted that within FIGS. 1, 2 and 3 of the drawings there are three in number of the transducer sections each of which includes a transducer plate 32. The third transducer section 32 located against the backing plate 24 is defined as EMAT #3, which is called out as box 87 in FIG. 6. EMAT #3 is to be constructed identically to EMATs #1 and #2. EMAT #3 has an arrangement of magnets 43 which is identical to magnets 42 and even are positioned the same as magnets 42. EMAT #3 is to be driven by an identical set of drive and receive electronics which have been previously discussed in relation to EMATs #1 and #2 which include an amplifier 83, transformer sensor 85, amplifier 89 and diode 91. The output from the diode 91 is transmitted to the analog-to-digital converter 96. The output of the signal generator 81 is also transmitted to the analog-to-digital converter 96 through line 99. The computer 78 transmits an output signal to signal generator 80 through line 95. The computer 78 also transmits an output signal through line 97 to the signal generator 81. The transducer sensor 85 is identical to sensors 90 and 100. The amplifier 89 is essentially identical to amplifiers 92 and 102. Also the diode 91 is essentially identical to the diodes 94 and 104. The amplifier 83 is essentially identical to the amplifiers 82 and 84. The only difference is the signal generator 81 has a different frequency range than the signal generator 80. Referring to FIGS. 7 and 9, it can be seen that regarding the signal generator 80, the frequency variation is about 2 KHz (in other words from a frequency of 587 KHz, the variation would be ±1 KHz). For the frequency generator 81 indicating a frequency of 587 KHz, the frequency would range from ±10 KHz. The purpose of EMAT #3 is, as previously mentioned, to adjust the overall frequency to compensate for temperature, hardness and stress. This adjustment is made by the computer 78. The sensed signals from EMAT #3 are transmitted to the computer 78. The precise center of the frequency range to be scanned is then determined. The 20 KHz range (±10 KHz) insures that the frequency will be picked up and not missed. As noted in FIGS. 7–9, the center is 587 KHz, but because of temperature, hardness and stress, this precise center may actually be anywhere between 577 KHz and 597 KHz. The center is determined by the graph of FIG. 7. The center of the scanned frequency will then be adjusted for EMATs #1 and #2.

Figure 4:
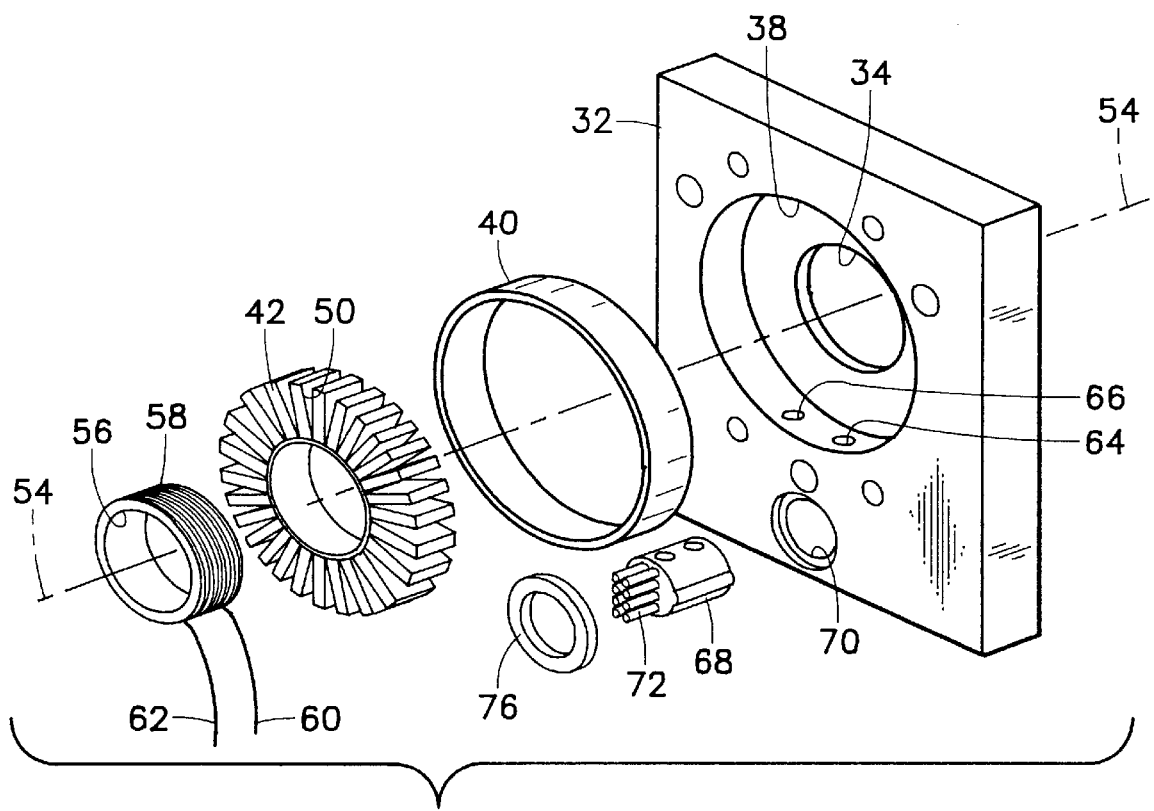
FIG. 4 is an exploded view of a single electromagnetic acoustic transducer included within the assembly of FIGS. 2 and 3.
Figure 10:
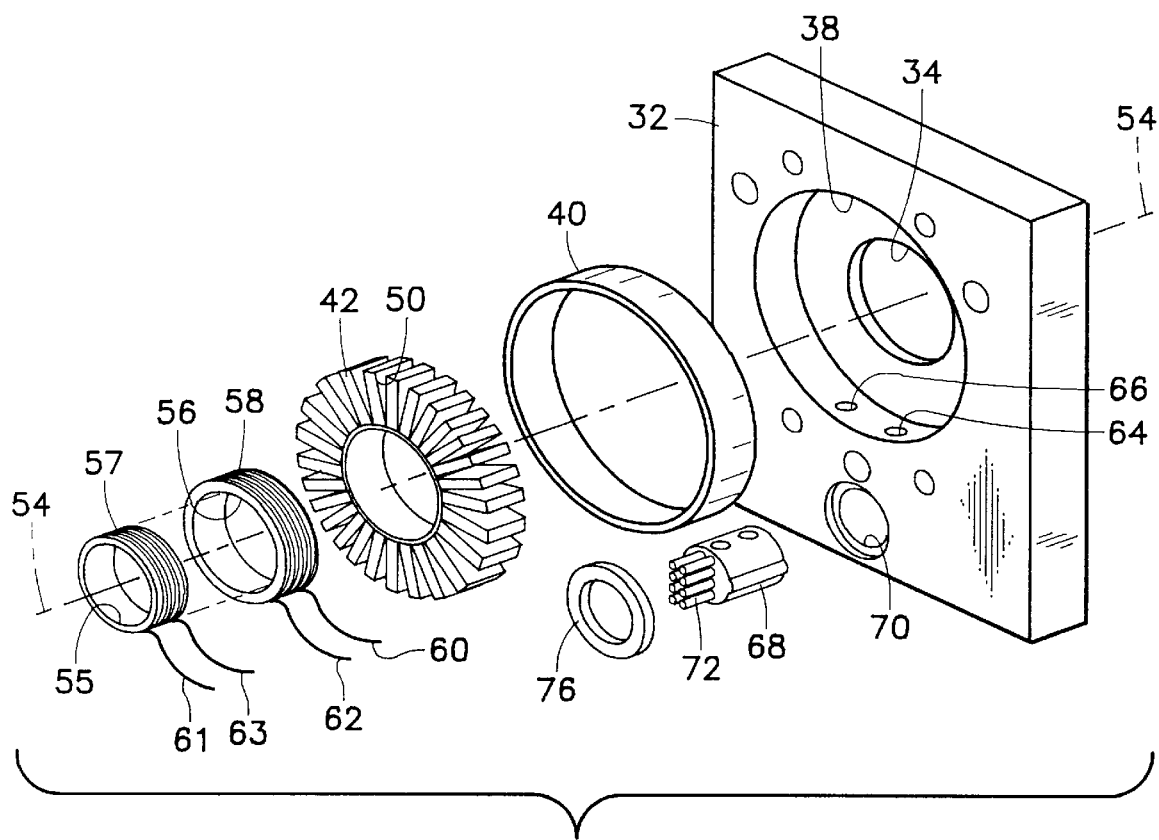
FIG. 10 is a view similar to FIG. 4 of a modified form of electromagnetic acoustic transducer which includes dual coils.

Referring particularly to FIG. 10 of the drawings, there is shown a modified form of an EMAT. This EMAT shown in FIG. 10 could be utilized for any of the EMATs shown in FIG. 6. Like numerals have been employed to refer to like parts. The only distinction in the construction of the EMAT in FIG. 10, when compared to FIG. 4, is that instead of a single wire coil 58 with leads 60 and 62, there is a second wire coil 57 mounted on a coil spool 55 which is located against the inside surface of the coil spool 56. The second wire coil 57 includes leads 61 and 63. Instead of using the separate EMATS #86 and #87 (or EMATs #88 and #87), the use of a single EMAT could be substituted for the two separate EMATs #86 and #87 with the wide band frequency range of ±10 KHz being transmitted to wire coil 57 and the narrow band of ±1 KHz being transmitted to wire coil 58.

What is claimed is:

1. The method of detecting a flaw in a metallic structure comprising the steps of:
    programming a computer with a flaw detection program for the metallic structure;
    calculating by a formula an unflawed first range of resonant frequencies for the metallic structure based on the specific individual physical characteristics of said metallic structure and supplying said frequencies into the computer;
    determining a second range of reasonable variance from said first range which would still qualify as an unflawed metallic member and supplying said variance into said computer;
    subjecting said metallic structure to the field of an electromagnetic acoustic transducer;
    moving said metallic structure through said field;
    discovering a frequency, if produced, that exceeds said second range which indicates a flaw in the metallic structure; and
    determining the position of the flaw in the metallic structure which will then permit non-use of the flawed area during manufacture of a metallic part from the metallic structure.

2. The apparatus as defined in claim 1 wherein:
    means for marking said metallic structure in the area of a flaw to thereby ascertain the position of said flaw.

3. In an apparatus for detecting flaws in a metallic structure with lineal relative movement to occur in a given direction between said apparatus and the metallic structure with the apparatus being spaced from the metallic structure, said apparatus comprising:
    an electromagnetic acoustic transducer constructed of a first array of magnets and a second array of magnets, said first array located directly adjacent said second array, both said first array and said second array being located transverse to said given direction, said first array of magnets comprising a plurality of first magnets mounted in an evenly spaced apart arrangement forming a first gap between each directly adjacent pair of said first magnets with there being a plurality of first gaps, said second array of magnets comprising a plurality of second magnets mounted in an evenly spaced apart arrangement forming a second gap between each directly adjacent pair of said second magnets with there being a plurality of second gaps, each of said second gaps is to be in alignment with one of said first magnets with said alignment being in a direction parallel to said given direction, each of said first gap is to be in alignment with one of said second magnets with said alignment being in a direction parallel to said given direction, whereby the metallic structure is to be moved directly adjacent said first and second array of magnets with a normal frequency range and output previously determined and upon a frequency output occurring which exceeds the frequency range in which a flaw in the metallic structure is indicated.

4. The apparatus as defined in claim 3 wherein:
    said electromagnetic acoustic transducer being spaced from said metallic structure thereby not contacting said metallic structure.

5. The apparatus as defined in claim 3 wherein:
    said first array of magnets being located in the shape of a first annulus, said second array of magnets being located in the shape of a second annulus.

6. The apparatus as defined in claim 5 wherein:
    said second array of magnets being identical in configuration to said first array of magnets.

7. The apparatus as defined in claim 6 wherein:
    said second array of magnets being positioned at an angular displacement relative to said first array of magnets.

8. The apparatus as defined in claim 7 wherein:
    said metallic structure having an exterior surface, each said magnet in said first array of magnets having a north pole and a south pole, each said magnet in said second array of magnets having a north pole and a south pole, a center axis connecting each said north pole and said south pole of each said magnet being located perpendicular to said exterior surface.

9. The apparatus as defined in claim 8 wherein:
    within both said first array of magnets and said second array of magnets said north and south poles alternate.

10. The apparatus as defined in claim 3 wherein:
    said metallic structure having an exterior surface, each said magnet in said first array of magnets having a north pole and a south pole, each said magnet in said second series of magnets having a north pole and a south pole, a center axis connecting each said north pole and said south pole of each said magnet being located perpendicular to said exterior surface.

11. The apparatus as defined in claim 10 wherein:
    within both said first array of magnets and said second array of magnets said north and south poles alternate.

12. In an apparatus for detecting flaws in a metallic structure with lineal relative movement to occur in a given direction between said apparatus and the metallic structure with the apparatus being spaced from the metallic structure, said apparatus comprising:
    an electromagnetic acoustic transducer constructed of a first transducer section, said first transducer section having a first array of magnets, a signal transmitter included within said first transducer section, said signal transmitter to receive a signal and then emit an electrical field in the presence of said first array of magnets, said metallic structure to be passed through said electric field, said signal transmitter comprising a plurality of separate coils of wire, each of said plurality of separate coils of wire to receive a different signal, whereby the metallic structure is to be moved directly adjacent said first array of magnets with the normal frequency range of an output previously determined and upon a frequency output occurring which exceeds the frequency range, a flaw in the metallic structure is indicated.

13. The apparatus as defined in claim 12 wherein:

there being a second transducer section located in a direction from said first transducer section which is parallel to said given direction, said second transducer section being substantially identical in construction to said first transducer section, said second transducer section having a second array of magnets, said second array of magnets being angularly displaced relative to said first array of magnets.

14. The apparatus as defined in claim 13 wherein:

said first array of magnets being located in the shape of a first annulus, a second array of magnets being located in the shape of a second annulus.

15. The apparatus as defined in claim 14 wherein:

said metallic structure having an exterior surface, each said magnet in said first array of magnets having a north pole and a south pole, each said magnet in said second array of magnets having a north pole and a south pole, a center axis connecting said north pole and said south pole of each said magnet being located perpendicular to said exterior surface.

16. The apparatus as defined in claim 15 wherein:

within both said first array of magnets and said second array of magnets said north and south poles alternate.

17. The apparatus as defined in claim 16 wherein:

means for marking said metallic structure in the area of a flaw to thereby ascertain the position of said flaw.

* * * * *